(12) United States Patent
Sommer et al.

(10) Patent No.: US 8,233,994 B2
(45) Date of Patent: *Jul. 31, 2012

(54) ACTIVE FIXATION MEDICAL LEAD

(75) Inventors: John L. Sommer, Coon Rapids, MN (US); Douglas N. Hess, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 606 days.

This patent is subject to a terminal disclaimer.

(21) Appl. No.: 12/420,326

(22) Filed: Apr. 8, 2009

(65) Prior Publication Data

US 2009/0192581 A1   Jul. 30, 2009

Related U.S. Application Data

(63) Continuation of application No. 11/186,551, filed on Jul. 21, 2005, now Pat. No. 7,532,939.

(51) Int. Cl.
*A61N 1/05* (2006.01)

(52) U.S. Cl. ........................................ 607/127

(58) Field of Classification Search ............... 607/127
See application file for complete search history.

(56) References Cited

U.S. PATENT DOCUMENTS

| | | | | |
|---|---|---|---|---|
| 5,076,285 | A * | 12/1991 | Hess et al. | 607/127 |
| 7,532,939 | B2 * | 5/2009 | Sommer et al. | 607/127 |
| 2002/0177772 | A1 * | 11/2002 | Altman et al. | 600/431 |

* cited by examiner

*Primary Examiner* — Kennedy Schaetzle

(74) *Attorney, Agent, or Firm* — Reed A. Duthler; Carol F. Barry

(57) ABSTRACT

An implantable medical device that includes an elongated body having a proximal end and a distal end, a helical fixation member extending from the distal end of the elongated body, the helical fixation member including a distal tip for affixing the distal end of the elongated body at an implant site, and a tracking member extending from the distal end of the elongated body, through the helical fixation member and outward from the distal tip of the helical fixation member for tracking along an implant pathway during implantation of the implantable medical device.

13 Claims, 17 Drawing Sheets ic Fixation Medical Lead

CROSS-REFERENCE TO RELATED APPLICATION

This application is a continuation of U.S. patent application Ser. No. 11/186,551 filed on Jul. 21, 2005, now issued as U.S. Pat. No. 7,532,939 on May 12, 2009. The disclosure of the above application is incorporated herein by reference.

TECHNICAL FIELD

The invention relates to implantable medical devices, particularly to configurations of elongated medical devices facilitating deployment to and fixation at an implant site.

BACKGROUND

In the medical field, implantable elongated medical devices, such as leads and catheters, are used with a wide variety of therapeutic or monitoring devices. For example, implantable leads are commonly used to form part of implantable cardiac pacemaker systems that provide therapeutic stimulation to the heart by sensing electrical activity of the heart and delivering pacing, cardioversion, or defibrillation pulses via electrodes disposed on the leads, typically near the distal ends of the leads. Elongated medical devices may also be used to deliver therapeutic agents. A number of challenges exist with respect to such medical devices, in particular, as more advanced and complex therapeutic techniques are developed, new configurations are required to facilitate deployment and fixation of elongated medical devices at targeted implant sites within a patient.

BRIEF DESCRIPTION OF THE DRAWINGS

Aspects and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION

The following detailed description provides a practical illustration for implementing various embodiments of the invention and is not intended to limit the scope, applicability, or configuration of the invention in any way.

Figure 1:
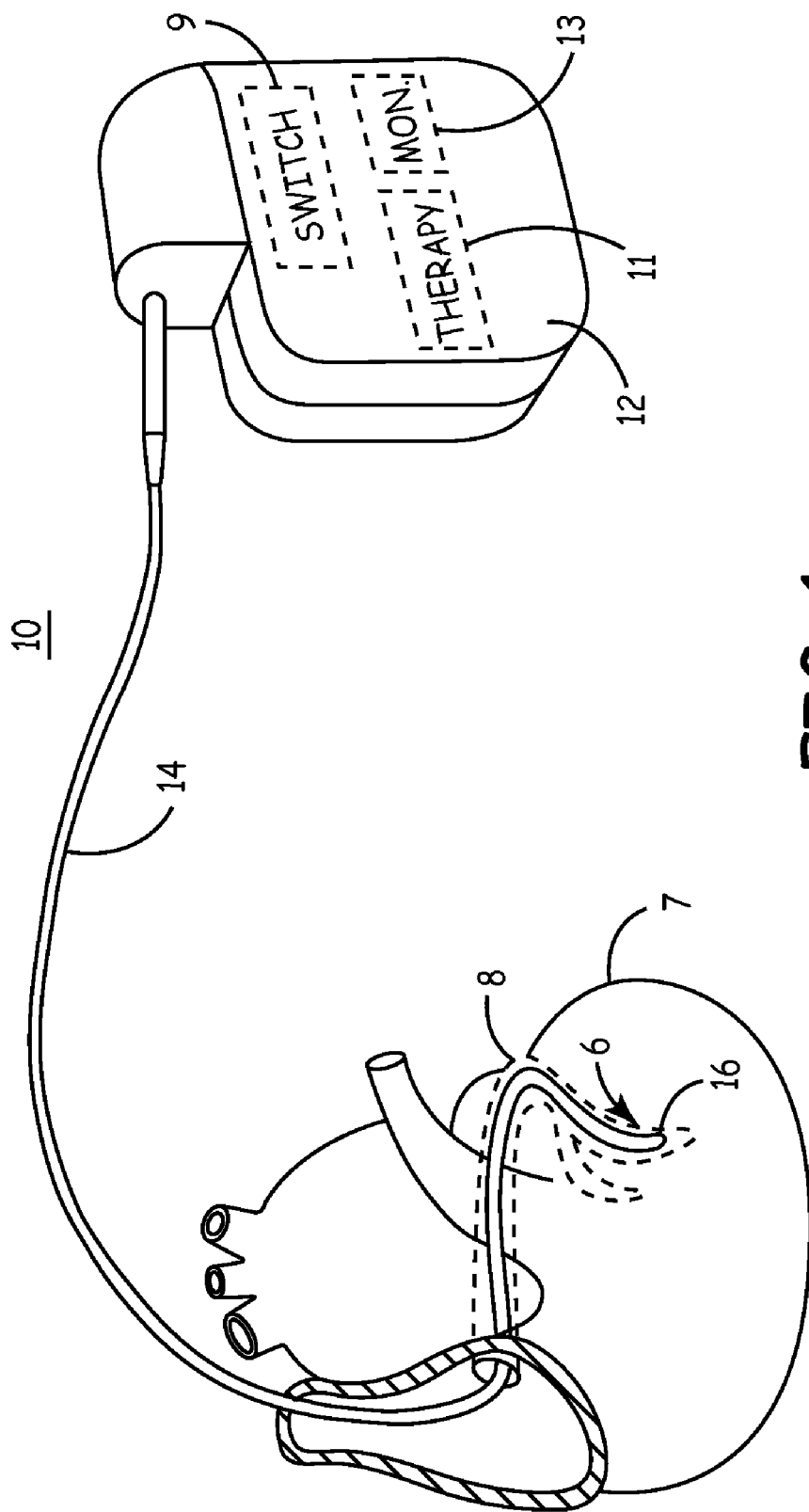
FIG. 1 is a schematic diagram of an implantable medical device according to an embodiment of the present invention.

FIG. 1 is a schematic diagram of an implantable medical device according to an embodiment of the present invention. As illustrated in FIG. 1, am implantable medical device 10 according to an embodiment of the present invention includes a cardiac therapy/monitoring device housing 12 and a lead 14, shown coupled to housing 12. Lead 14 is provided with a distal end 16, configured to facilitate fixation within a blood vessel at a targeted implant site so that a therapy can be delivered through lead 14 to a heart 7 from housing 12. Housing 12 includes circuitry for enabling device 10 to be capable of delivering pacing, cardioversion and/or defibrillation therapy to a patient via electrodes disposed on lead 14. As such, housing 12 includes a therapy delivery module 11 which includes the electrical circuitry to generate stimulation pulses and control the timing and delivery of electrical stimulation pulses. Such circuitry is well known in the art of cardiac pacemakers. Housing 12 further includes monitoring module 13 for monitoring physiological signals received by lead 14, and may further include switching circuitry 9 for facilitating selection of various electrodes available on lead 14 for sensing cardiac signals and/or for delivering stimulation therapy. Electrode-selecting switching circuitry is known in the art.

Embodiments of the present invention are not limited for use in electrical stimulation therapy delivery. Therapy delivery module may alternatively or additionally include a drug pump for administering a pharmaceutical, biologic or genetic agent. As such, lead 14 may include a fluid delivery lumen coupled to therapy/monitoring device 12. Lead 14 may additionally or alternatively include physiological sensors for gathering physiological data for patient monitoring purposes by monitoring module 13. Devices that integrate monitoring and therapy delivery features, along with connection means for associated leads, are well known to those skilled in the art.

As illustrated in FIG. 1, lead 14 is used as a coronary sinus lead, implanted in a cardiac vein 8 via the coronary sinus and fixed at a corresponding left ventricular epicardial site 6 of the heart 7. As used herein "coronary sinus lead" refers to a lead implanted in the cardiac vasculature via the coronary sinus, which can include any cardiac vein branch. According to embodiments of the present invention, distal end 16 of lead 14 includes a fixation element and tracking member extending therefrom, to facilitate deployment of lead 14 and fixation at the illustrated implant site. Distal end 16, as will be illustrated by the various embodiments described herein, is configured to allow fixation of an elongated medical device, such as the coronary sinus lead 14 shown in FIG. 1 or other leads or catheters, within a generally tubular organ such as a blood vessel. Implant sites made more viable by embodiments of the present invention include those accessed by implantation of an elongated medical device in any cardiac vein. Furthermore, embodiments of the present invention are not limited to cardiac or vascular implantation sites but may also find use in other locations in a body, for example for neuro-stimulation or drug or biological fluid delivery.

Figure 2:
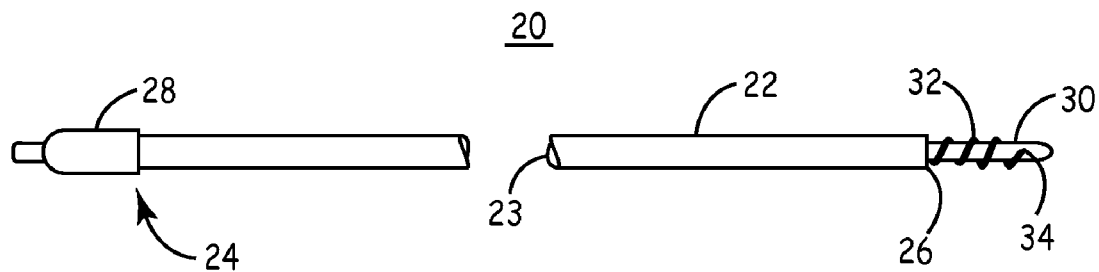
FIG. 2 is a plan view of an elongated medical device according to an embodiment of the present invention.

FIG. 2 is a plan view of an elongated medical device according to an embodiment of the present invention. As illustrated in FIG. 2, according to an embodiment of the present invention, an elongated medical device 20, which may be embodied as the coronary sinus lead 14 shown in FIG. 1, includes an elongated body 22 having at least one lumen 23 extending between a proximal end 24 and a distal end 26 of elongated body 22. Proximal end 24 may be provided with a connector assembly 28 for use in coupling elongated device 20 to an implantable monitoring/therapy delivery device. For example, elongated device 20 may be electrically coupled to a cardiac stimulation device, such as a pacemaker or cardioverter/defibrillator. In alternative embodiments, proximal end 24 of elongated device 20 may be configured for connection to a drug pump, neuro-stimulator, or other monitoring or therapy delivery device.

A helical fixation member 32 is provided extending from the distal end 26 of elongated body 22. Helical fixation member 32 is adapted for actively fixing the distal end 26 of elongated device 20 at a desired implant site. As such, helical fixation member 32 is provided with a tissue-piercing distal tip 34.

A tracking member 30 also extends from the distal end 26 of elongated body 22, with helical fixation member 32 extending about tracking member 30 so that tracking member 30 extends through helical fixation member 32 with a distal end of tracking member 30 extending distally outward from tissue-piercing distal tip 34. The distance that tracking member 30 extends outward form tissue-piercing distal tip 34 can vary between embodiments and could range, for example, from a fraction of a centimeter to several centimeters. Tracking member 30 facilitates tracking of elongated medical device distal end 26 along an implant pathway and is therefore referred to herein as a "tracking member" for the sake of convenience. However, tracking member 30 can also serve other functions as will become apparent from the following description and is not limited to performing tracking functions per se. For example, tracking member 30 also acts to prevent catching or snagging of tissue-piercing distal tip 34 on body tissue or anatomical features during advancement of elongated medical device 20 to an implant site.

Figure 3:
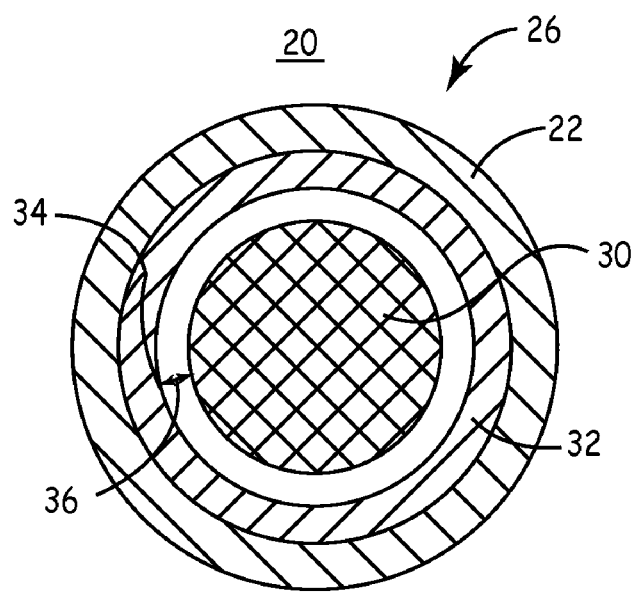
FIG. 3 is an end view of the elongated device shown in FIG. 2.

FIG. 3 is an end view of elongated device 20. Another function of tracking member 30 is to cooperate with helical fixation member 32 to engage tissue between fixation member 32 and tracking member 30 upon rotation of fixation member 32 within body tissue during fixation of helical member 32 at an implant site. As such, at least a portion of the distal windings of helical fixation member 32 are proportioned relative to the adjacent outer surface of tracking member 30 so that fixation member 32 is positioned a distance 36 from tracking member 30 to form a gap between fixation member 32 and tracking member 30. Body tissue at the implant site becomes engaged or "sandwiched" within the gap between helical fixation member 32 and tracking member 30 when helical fixation member 32 is rotated into the body tissue at the implant site to fix distal end 26 of elongated medical device 20.

Distance 36 that fixation member 32 is spaced from tracking member 30 controls the depth that helical fixation member 32 penetrates into the body tissue at the implant site. The length of distance 36 between fixation member 32 and tracking member 30, as well as the linear distance along tracking member 30 that distance 36 extends will vary between embodiments and will depend on various design considerations such as the anatomical location and type of tissue in which helical fixation member 32 is implanted and other relative dimensions of fixation member 32 and tracking member 30. Distance 36 may range in size, for example, from approximately 0.005 inches to approximately 0.02 inches, but is not limited to this range. According to an embodiment of the present invention, fixation member 32 is spaced distance 36 from tracking member 30 along the entire length of fixation member 32. However, according to another embodiment of the present invention, fixation member 32 is spaced distance 36 from tracking member 30 along only a distal portion of fixation member 32, with the outer diameter of tracking member 30 being approximately equal to the inner diameter of fixation member 32 (i.e., distance 36 is approximately zero) along a proximal portion of fixation member 32. The linear distance that space 36 extends along the distal portion of helical fixation member 32 may range from approximately one millimeter to several centimeters, depending on the overall length of helical fixation member 32 and the particular application.

In the example of the coronary sinus lead embodiment of FIG. 1, helical fixation member 32 may be provided having a 4 French diameter with tracking member having an outer dimension of approximately 0.04 inches so that distance 36 between tracking member 30 and fixation member 32 is approximately 0.01 inches. Helical fixation member 32 and corresponding tracking member 30 may be provided with different diameters for use in cardiac veins of different sizes. Distance 36 may extend, for example, for approximately 0.25 cm to approximately 1 cm along a linear distance of the distal portion of helical fixation member 32 included in a coronary sinus lead.

Figure 4A:
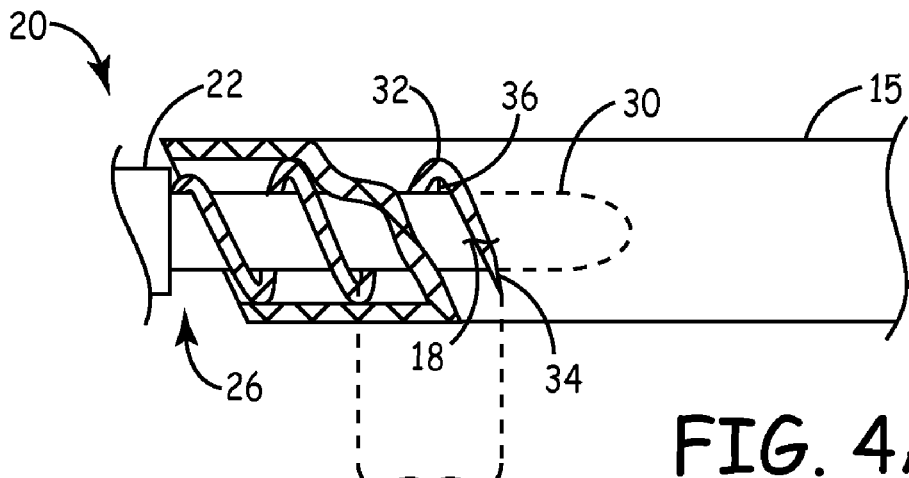
FIG. 4A is a schematic diagram of a distal end of an elongated medical device implanted in a blood vessel according to an embodiment of the present invention.
Figure 4B:
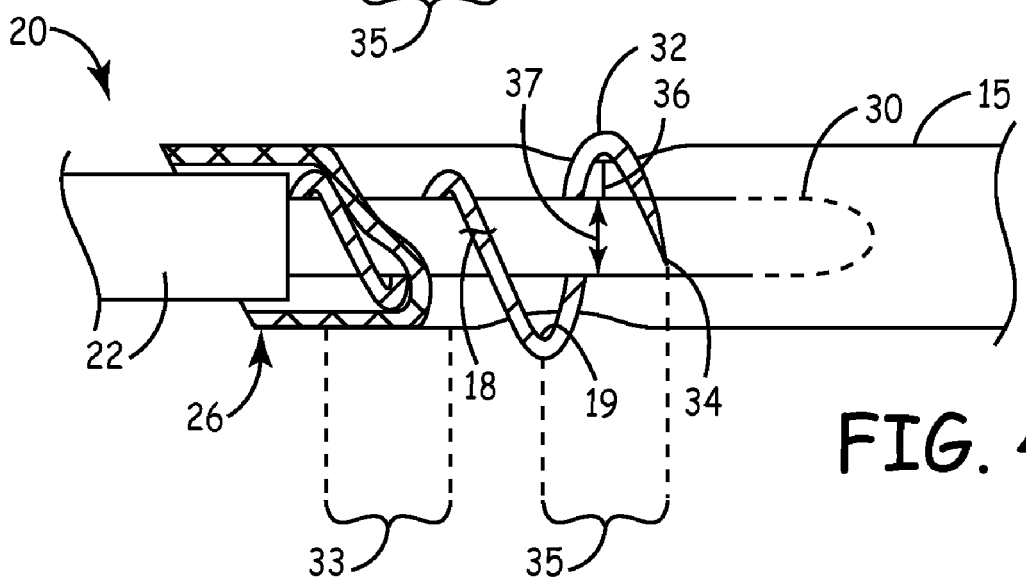
FIG. 4B is a schematic diagram of the engagement of implant-site tissue between a helical fixation member and a tracking member extending from a distal end of an elongated medical device, according to an embodiment of the present invention.

FIG. 4A is a schematic diagram of a distal end of an elongated medical device implanted in a blood vessel according to an embodiment of the present invention. FIG. 4B is a schematic diagram of the engagement of implant-site tissue between a helical fixation member and a tracking member extending from a distal end of an elongated medical device, according to an embodiment of the present invention. FIGS. 4A and 4B illustrate the engagement of implant-site tissue between helical fixation member 32 and tracking member 30 according to an embodiment of the present invention. In FIG. 4A, the distal end 26 of elongated medical device 20 is shown implanted in a blood vessel 15. In some applications, blood vessel 15 is a cardiac vein. Distal winding 35 of helical fixation member 32 is shown having an inner diameter greater than the outer diameter of tracking member 30 such distal winding 35 is spaced distance 36 from tracking member 30. Elongated device body 22 is provided with adequate torsional stiffness so as to translate rotational movement applied at its proximal end to the distal end 26 to thereby cause rotation of helical fixation member 32. As elongated medical device 20 is advanced along an implant pathway, body 22 may be counter-rotated (i.e., rotated in a direction opposite that required to affix helical fixation member in tissue) to prevent tissue-piercing distal tip 34 from catching or snagging on body tissue or anatomical features.

When tracking member 30 is positioned at a desired implant site, elongated medical device 20 is rotated at its proximal end by the implanting clinician, causing tissue-piercing distal tip 34 of helical fixation member 32 to pierce into blood vessel 15. In the example shown, distal tip 34 penetrates through the wall of blood vessel 15 at site 18. In a cardiac vein application, distal tip 34 may penetrate through the wall of vessel 15 into surrounding myocardial tissue. In practice, distal tip 34 may pierce into a targeted blood vessel wall, or any other body tissue at the fixation site, with or without fully penetrating through the tissue, depending on the tissue thickness and relative size of helical fixation member 32 and tracking member 30 and the corresponding tissue-engaging space 36 formed there between.

As shown in FIG. 4B, further rotation of elongated device 20 causes helical fixation member 32 to advance through piercing site 18 such that a segment 19 of blood vessel 15 becomes engaged in the gap formed by distance 36 between helical fixation member 32 and tracking member 30. Distance 36 between tracking member 30 and helical fixation member 32 for engaging implant-site tissue between helical fixation member 32 and tracking member 30 is provided linearly along all or at least a portion of helical fixation member windings, extending proximally from tissue-piercing distal tip 34, by forming at least a portion of the windings with a larger diameter than the adjacent outer diameter 37 of tracking sleeve 30.

As illustrated in FIGS. 4A and 4B, the diameter of the inner surface of helical fixation member 32 is approximately equal to the diameter of tracking member 30 along proximal winding 33 of helical fixation member 32 so that there is no longer a gap formed by distance 36 along proximal winding 33. In this way, proximal winding 33 acts as a mechanical stop against further advancement of fixation member 32 into vessel 15. As tissue engaged within gap form by distance 36 reaches proximal winding 33, further proximal advancement of tissue between helical fixation member 32 and tracking member 30 is inhibited, resulting in greater resistance being met with further rotation of elongated device 20. Torque is built up on elongated device body 22 providing tactile feedback to the clinician that the distal end 26 is fixed. The torsional stiffness of elongated device body 22 is designed to provide translation of rotational movement from the proximal end to distal end 26 of device 20 during advancement and fixation of distal end 26 and to provide tactile feedback of torque build-up when helical fixation member is fully fixed in body tissue at the implant site. In one embodiment, elongated device body 22 is formed from 55D polyurethane, however, other durometer materials may provide acceptable torsional stiffness for translating proximal to distal rotational motion and distal to proximal torque feedback.

By providing of tracking member 30 extending through helical fixation member 32, and spaced distance 36 from helical fixation member 32 along at least the distal portion 35 of the windings so that tissue is advanced between helical fixation member 32 and tracking member 30 during rotation of the elongated device 20 promotes parallel or substantially concentric tracking of the blood vessel 15 by helical fixation member 32 during fixation of member 32 to control the depth of penetration within the surrounding tissue by helical fixation member 32. In cardiac vein applications, limiting the position of the helical fixation member 32 to within or proximate the vein wall reduces the likelihood of inadvertently piercing a nearby artery during fixation of member 32.

Figure 5:
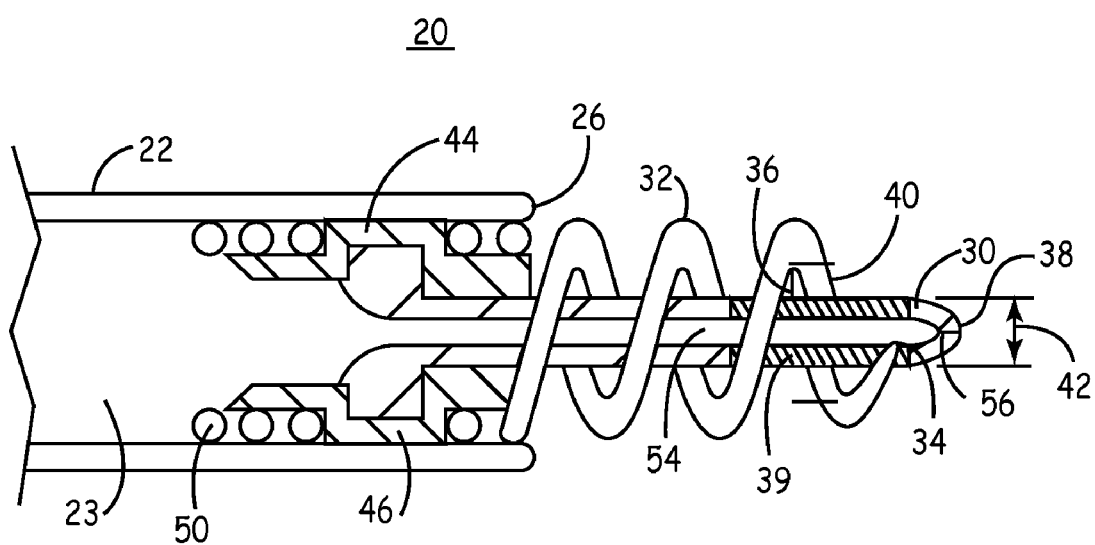
FIG. 5 is a sectional view of the distal end of the elongated medical device shown in FIG. 2, which illustrates one configuration of a helical fixation member and a tracking member.

FIG. 5 is a sectional view of the distal end of elongated medical device 20, which illustrates one configuration of a helical fixation member and a tracking member. Helical fixation member 32 is shown having a fixed winding diameter 40 greater than the outer diameter 42 of tracking member 30 so that tracking member 30 is spaced distance 36 from helical fixation member 32 for the entire length of helical fixation member that extends from distal end 26 of elongated body 22. Tracking member 30 can be formed as a molded component, typically fabricated from a polymer material such as silicone or polyurethane.

As illustrated in FIG. 5, according to an embodiment of the present invention, tracking member 30 is fixed to a welding sleeve 44 used in assembling elongated medical device 20. Welding sleeve 44 is adhesive bonded or otherwise fixed within elongated medical device body 22, near distal end 26. Welding sleeve 44 is shown having a channel 46 on its inner diameter to accommodate tracking member 30. Tracking member 30 may be molded into welding sleeve 44 or compression fit and/or adhesive bonded to welding sleeve 44. Tracking member 30 is thereby fixedly coupled to elongated medical device body 22 via welding sleeve 44.

Helical fixation member 32 is welded to the outer diameter of welding sleeve 44. In some embodiments, helical fixation member 32 functions additionally as an electrode for sensing electrical body signals or for delivering an electrical stimulation therapy. As such, helical fixation member 32 is formed of a conductive material, such as platinum, iridium, a platinum-iridium alloy, stainless steel or other material known for use in fabricating implantable electrodes. Welding sleeve 44 is likewise formed from a conductive material and provides electrical coupling between helical fixation member 32 and a conductor 50, shown in FIG. 5 as a coiled conductor. Conductor 50 extends from welding sleeve 44 to the proximal end of elongated medical device 20 through lumen 23 where it is coupled to a connecter assembly according to methods known in the art.

According to an embodiment of the present invention, tracking member 30 may be adhesively bonded directly to the elongated body 22. If helical fixation member 32 is not intended for use as an electrode, welding sleeve 44 is not required for providing electrical coupling of fixation member 32 to a conductor. As such, a configuration of distal end 26 may include helical fixation member 32 and tracking member 30 bonded to distal end 26 without the use of welding sleeve 44.

Tracking member 30 is shown as a hollow member having an open lumen 54. Elongated body 22 is provided with a lumen 23 that is in communication with tracking member lumen 54. Tracking member 30 includes a distal opening 56 to enable an elongated member or fluid agent to be passed through elongated body lumen 23, tracking member lumen 54 and out distal end 38 of tracking member 30. As will be described in greater detail below, elongated medical device 20 may be deployed over a guide wire to a desired implant site. A previously placed guide wire can pass through opening 38 as elongated device 20 is advanced over the guide wire to a targeted implant site.

In certain embodiments, elongated medical device 20 may be used as a fluid delivery catheter or in conjunction with a drug pump for local administration of a biological, pharmacological, or genetic material in a fluid agent. The fluid agent may be delivered through body lumen 23 and tracking member lumen 54 through opening 56 into the surrounding body tissue and/or fluids. A micro-catheter or needle used for administering the fluid agent may be passed through body lumen 23, tracking member lumen 54 and out tracking member distal end 38 through opening 56. It is recognized that tracking member 30 may be provided with multiple passages through which a fluid agent may exit the distal end of elongated medical device 20.

Opening 56 is provided as a sealing passage that forms a fluid-tight or fluid-resistant seal around an elongated member or device passing there through to prevent the back flow of blood or other body fluids into elongated body lumen 23. Alternatively opening 56 may be provided as an open passage that does not resist the back flow of body fluids into body lumen 52.

It is recognized that in some applications, passage of a device or fluid agent through tracking member 30 may be unnecessary. In corresponding embodiments, tracking member 30 may be provided without opening 56 or as a solid member, without lumen 54.

In any of the various embodiments described herein, tracking member 30, or any portion thereof, may be provided as a drug-eluting member. A drug eluting portion 39 may be formed from or coated with a polymeric material adapted for doping with a pharmacological or biological agent, such as a steroid or other anti-inflammatory or an antibiotic agent, intended for elution into the body tissue or body fluids at the implant site. Methods for incorporating a drug in a medical lead for elution after implantation are known in the art. Reference is made, for example, to U.S. Pat. No. 5,265,608, incorporated herein by reference in its entirety.

Figure 6:
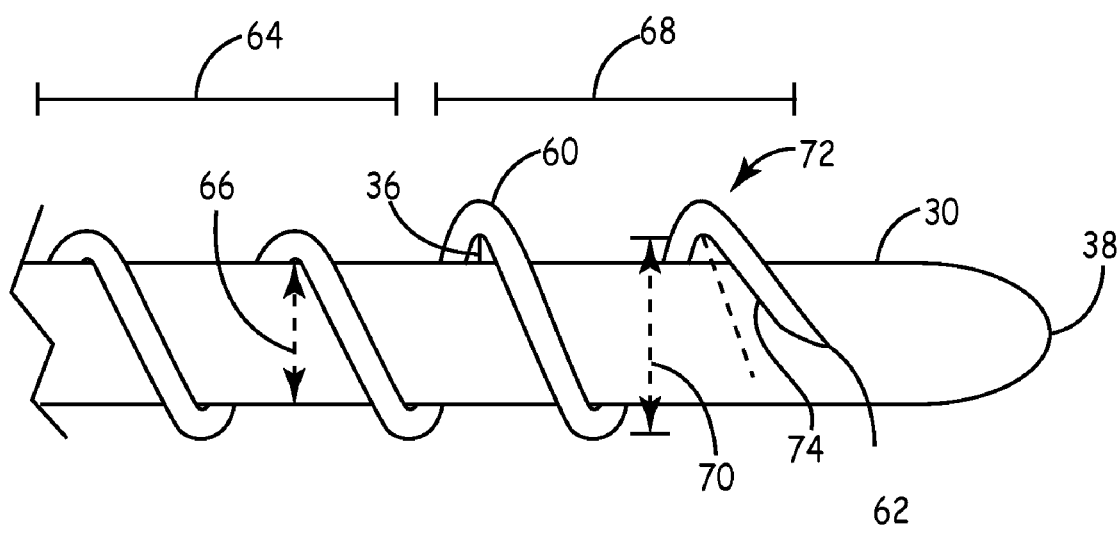
FIG. 6 is a schematic diagram of a helical fixation member and a tracking member according to an embodiment of the present invention.

FIG. 6 is a schematic diagram of a helical fixation member and a tracking member according to an embodiment of the present invention. As illustrated in FIG. 6, a helical fixation member 60 according to an embodiment of the present invention includes a fixed diameter 66 across proximal windings 64 such that proximal windings 64 are supported on their inner diameter by tracking member 30. Proximal winding diameter 66 is approximately equal to the outer dimension of tracking member 30. Distal windings 68 of helical fixation member 60 are formed with a diameter 70 that is larger than the outer diameter of fixation member 30 so that tracking member 30 is spaced distance 36 from helical fixation member 60 to form a tissue engaging gap, as described above. Thus, according to an embodiment of the present invention, helical fixation member 32 is formed with a step increase in winding diameter so as to be correspondingly spaced from fixation member 60. The step increase in winding diameter may occur anywhere along helical fixation member proximal to tissue-piercing tip 62.

The proximal windings 64 having a smaller winding diameter create a physical stop against body tissue engaged in space 36. As helical fixation member 32 is rotated into implant site tissue, torsional resistance will increase as the tissue engaged in the gap formed by distance 36 between fixation member 60 and tracking member 30 reaches the smaller proximal windings, thereby providing tactile feedback to a clinician that fixation member 32 is fixated in the tissue.

In FIG. 6, the distal portion of the final distal winding 72 is shown canted at an angle 74 relative to the normal pitch of distal windings 68, causing distal tip 62 of helical fixation member 60 to be angled more toward the distal end 38 of tracking member 30. In some embodiments, a canted distal tip 34 is provided so that upon rotation of the elongated medical device, tissue-piercing distal tip 62 readily engages and enters the body tissue at the implant site. Tissue-piercing distal tip 62 can be provided with a beveled or sharpened edge to ease entry into the tissue.

Figure 7A:
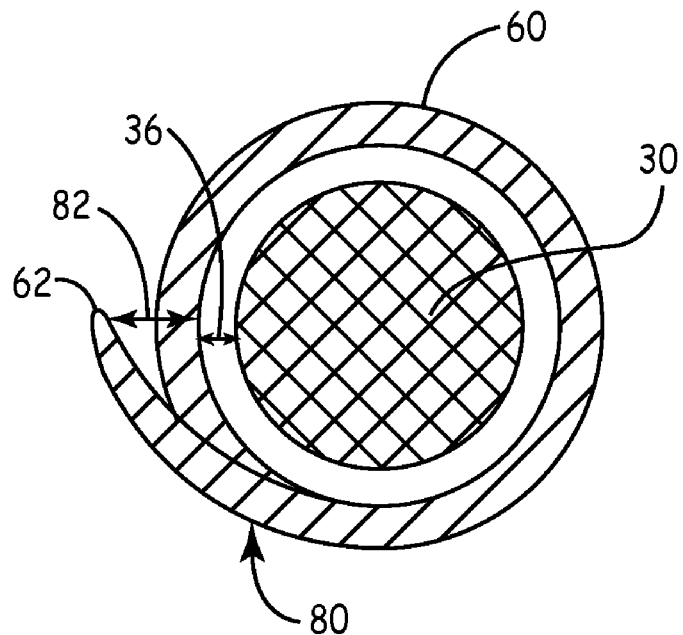
FIG. 7A is an end view of an elongated medical device illustrating one configuration of the tissue-piercing distal tip of the helical fixation member.

Other variations in the spatial arrangement of tissue piercing distal tip 62 relative to the remainder of helical fixation member 60 and tracking member 30 may be provided to facilitate engagement and entry of tissue-piercing distal tip 62 into a targeted tissue. FIG. 7A is an end view of an elongated medical device illustrating one configuration of the tissue-piercing distal tip of the helical fixation member according to an embodiment of the present invention. Tracking member 30 is shown extending through helical fixation member 60 spaced distance 36 from tracking member 60 along at least a distal portion of helical fixation member 60. The final distal winding 80 of helical fixation member 60 is shown having a non-concentric winding diameter causing distal tip 62 of helical fixation member 60 to extend outward an additional distance 82 from tracking member 30.

Upon rotation of the elongated medical device, distal tip 62 will pierce the tissue at the implant site. The outward extension of distal tip 62 created by the non-concentric winding diameter of distal winding 80 facilitates engagement and entry of tip 62 into body tissue at the implant site, for example into a cardiac vein wall. In particular applications, the relation of tissue-piercing distal tip 62 relative to the winding diameter and pitch of helical fixation member 60 and relative to the tracking member 30 may vary in order to enhance the engagement and entry of distal tip 62 into body tissue at a targeted implant site upon rotation of the elongated medical device.

Figure 7B:
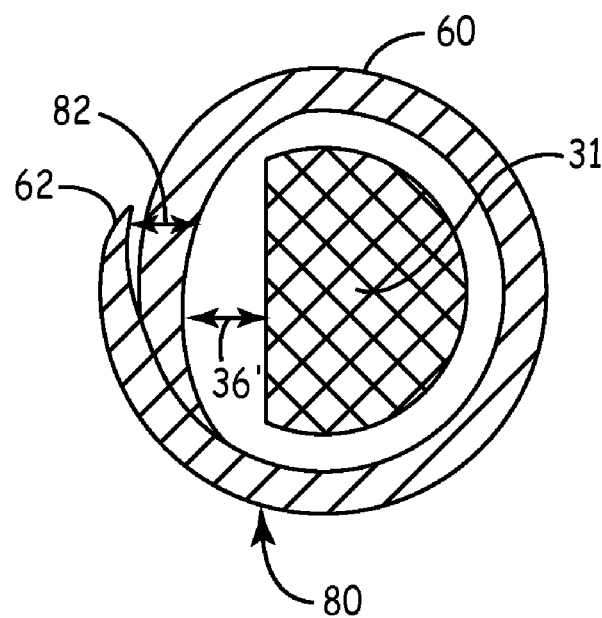
FIG. 7B is an end view of a tracking member having a non-circular cross-section resulting in a non-uniform tissue-engaging space between the tracking member and the helical fixation member.

Distance 36 may or may not be uniform in cross-section. For example, according to an embodiment of the present invention, tracking member 30 may be provided with a generally circular cross-section as shown in FIG. 7A so that distance 36 between fixation member 60 and tracking member 30 is generally symmetrical around tracking member 30. However, in some embodiments, a tracking member may be provided with a non-circular cross-section to form a generally non-symmetrical or non-uniform distance 36 between fixation member 60 and tracking member 30. FIG. 7B is an end view of a tracking member 31 according to an embodiment of the present invention having a non-circular cross-section resulting in a non-uniform distance 36' between fixation member 60 and tracking member 31. Such a non-uniform distance 36' results in greater penetration of fixation member 32 on one side of tracking member 31 than on the other. Preferentially greater penetration of helical fixation member 60 in a given direction at the implant site may allow more optimal fixation in a targeted tissue for a particular therapy delivery. For example, in the cardiac vein application, deeper penetration into the left ventricular myocardium may be desired with less penetration on the outer surface of the cardiac vein. Preferentially greater penetration of helical fixation member 60 in a given direction at the implant site may also allow a delicate anatomical feature to be avoided, such as a nerve or artery, while still allowing secure fixation of helical fixation member 60. Non-circular tracking member 31 is shown having a generally "D" shaped geometry, however, it is appreciated that a tracking member may be provided with a variety of cross-sectional geometries without departing from the scope of the invention.

Figure 8:
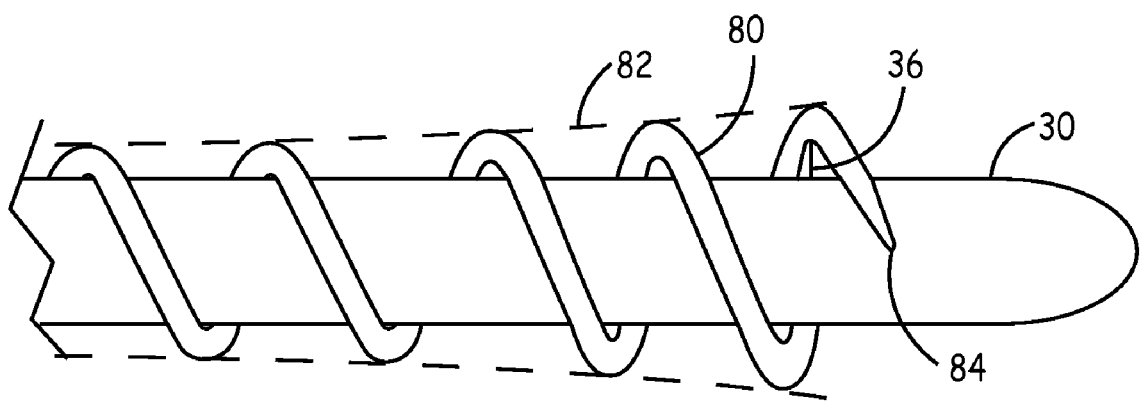
FIG. 8 is a schematic diagram of a helical fixation member and corresponding tracking member according to an embodiment of the present invention.
Figure 9:
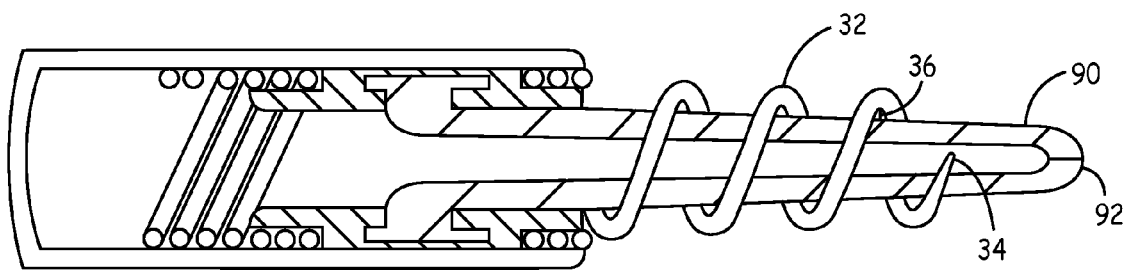
FIG. 9 is a schematic diagram of a helical fixation member and tracking member according to yet another embodiment.
Figure 10:
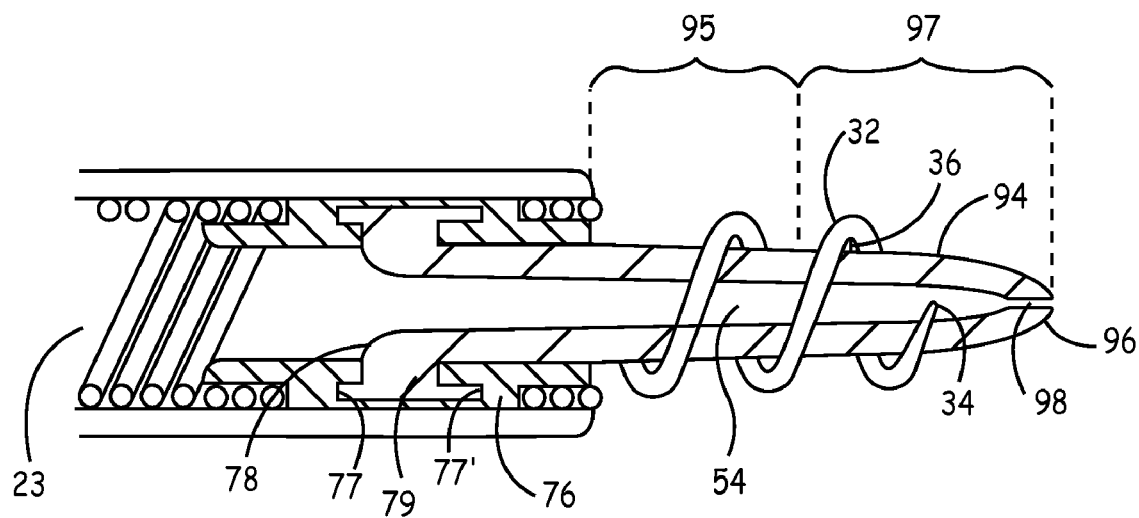
FIG. 10 is a schematic diagram of a tracking member having a fixed outer diameter along a proximal portion and a tapering or decreasing diameter along a distal portion according to an embodiment of the present invention.

FIGS. 8, 9 and 10 illustrate alternative configurations of a helical fixation member and corresponding tracking member for creating a tissue-engaging space there between. In FIG. 8, distance space 36 between tracking member 30 and fixation member 80 is created by fabricating helical fixation member 80 with a variable winding diameter 82 that increases in the direction of tissue-piercing distal tip 84. The variable winding diameter 82 is continuously increasing so that distance 36 that the distal windings of helical fixation member 80 are spaced from tracking member 30 increases from the proximal end of the distal windings to the distal end of the distal windings.

Upon rotation of the elongated medical device, tissue-piercing distal tip 84 enters the tissue at the implant site and helical fixation member becomes fixed within the targeted tissue. A layer of tissue will be engaged within the gap formed by distanced 36 between tracking member 30 and fixation member 80. As fixation member 80 is advanced further into the implant site tissue, greater resistance will be met as the gap formed by distance 36 between tracking member 30 and fixation member 80 becomes smaller adjacent proximal windings of helical fixation member 80. The increasing resistance provides tactile feedback to an implanting clinician that the helical fixation member is engaged with the tissue at the implant site.

FIG. 9 is a schematic diagram of a helical fixation member and tracking member according to an embodiment of the present invention. As illustrated in FIG. 9, according to an embodiment of the present invention, helical fixation member 32 is provided with a constant winding diameter, while tracking member 90 is provided with a tapered geometry. The outer diameter of tracking member 90 decreases moving toward distal end 92 of tracking member 90 creating a variation in distance 36 between helical fixation member 32 and tracking member 90.

As illustrated in FIG. 10, according to an embodiment of the present invention, tracking member 94 is formed having a fixed outer diameter along a proximal portion 96 and a tapering or decreasing diameter along a distal portion 97. Helical fixation member 32 is provided with a constant winding diameter thereby creating a tissue-engaging gap corresponding to distance 36 along the tapering, distal portion 97 of tracking member 94. In alternative embodiments, the tracking member 94 may be provided with a step-wise decrease in diameter at any point along its length proximal to the tissue-piercing distal tip of the helical fixation member 32 to create a tissue-engaging gap corresponding to distance 36 between a distal portion of helical fixation member 32 and the tracking member 94.

It is recognized that numerous configurations of a helical fixation member and a corresponding tracking member extending there through can be conceived for creating a tissue-engaging space between the fixation member and the tracking member beginning at the tissue-piercing distal tip of the fixation member and extending proximally from the tip for at least a portion of the length of the fixation member. As such, the scope of the invention is not intended to be limited to the specific configurations shown in the accompanying drawings. Indeed, the tissue-engaging gap formed by distance 36 may be constant or variable in cross-section moving proximally from the tissue-piercing distal tip of the fixation member. Associated geometries of a helical fixation member and associated tracking member for forming a tissue-engaging space there between may include constant or variable dimensions, which change in a gradual or step-wise manner, as illustrated by the example embodiments shown in FIGS. 5 through 10.

Welding sleeve 76 is shown in FIG. 10 with a proximal undercut groove 77 and distal undercut groove 77' extending from the channel 79 provided for holding tracking member 94. Proximal undercut groove 77 promotes stability of the mechanical coupling between tracking member 94 and welding sleeve 76 when forces are exerted against tracking member distal end 96. Distal undercut groove 77' promotes stability of the mechanical coupling between tracking member 94 and welding sleeve 76 when forces are exerted against proximal face 78 of tracking member 94. Forces may be exerted against proximal face 78 when an elongated member such as a guide wire, stylet, microcatheter or needle is advanced through body lumen 23. Proximal face 78 is shown chamfered to promote unobstructed advancement of an elongated member through lumen 23 into tracking member lumen 54 and out passage 98 at tracking member distal end 96. It is recognized that welding sleeve 76 may be designed with varying geometries to promote a stable mechanical coupling between welding sleeve 76 and tracking member 94.

Figure 11:
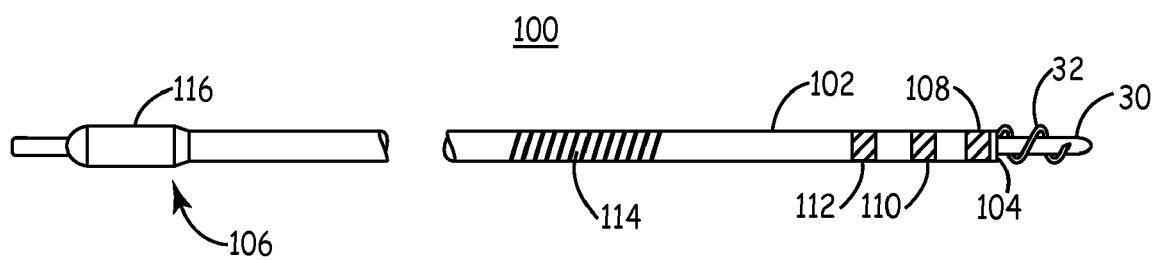
FIG. 11 is a plan view of a medical electrical lead according to an embodiment of the present invention.

FIG. 11 is a plan view of a medical electrical lead according to an embodiment of the present invention. As illustrated in FIG. 11, according to an embodiment of the present invention, lead 100 includes an elongated lead body 102 having helical fixation member 32 extending from distal lead body end 104. Tracking member 30 extends through helical fixation member 32 as described above. Lead 100 is provided with one or more electrodes for use in sensing electrical body signals and/or delivering an electrical stimulation therapy. Lead 100 is shown having multiple ring electrodes 108, 110 and 112 and a coil electrode 114. In addition, helical fixation member 32 may serve as an electrode. Electrodes 108, 110, 112, and 114 and fixation member 32 are coupled to insulated conductors extending from each corresponding electrode to proximal lead end 106 for electrical coupling to a connector assembly 116 according to arrangements and methods known in the art.

In some embodiments, helical fixation member 32 and one or more of ring electrodes 108, 110 and 112 may be configured in a multi-cathodal arrangement. Each of fixation member 32 and electrodes 108, 110, and 112 are coupled to separate, insulated conductors and can be selectively coupled to circuitry included in an associated medical electrical stimulation device. As such, if the sensing or stimulation performance obtained using, for example, fixation member 32 is unacceptable, one of electrodes 108, 110 or 112 may be selected to achieve better lead performance. In other embodiments, electrodes 108, 110 and 112 and fixation member 32 may be configured in any bi-polar or multi-polar electrode arrangement. Electrode selection for sensing and/or stimulation is performed using switching circuitry 9 (shown in FIG. 1) included in an associated therapy/monitoring device.

In one particular example in which lead 100 is used as cardiac vein lead, one or more electrodes 108, 110 and 112 and helical fixation member 32 may be provided as selectable cathode electrodes. In some instances, undesired phrenic nerve stimulation occurs when pacing pulses are delivered to the left ventricle of the heart using a cardiac vein lead. When lead 100 is implanted in a cardiac vein and fixed at a desired implant site using helical fixation member 32, phrenic nerve stimulation that may occur using one of fixation member 32 or electrodes 108, 110, or 112 may be avoided by selecting a different one of fixation member 32 or electrodes 108, 110, or 112 as an alternative cathode electrode.

Lead 100 is also shown to include coil electrode 114. Coil electrode 114 is typically used for high-voltage stimulation applications such as for delivering a cardioversion or defibrillation shock to a patient's heart. Coil electrode 114 may alternatively be used for sensing and/or low-voltage stimulation application in combination with any of the other electrodes 108, 110 and 112 or fixation member 32 carried by lead 100 or any other electrodes included in an implanted lead system. It is appreciated that in various embodiments, lead 100 may be equipped with other types of electrodes or physiological sensors.

Figure 12:
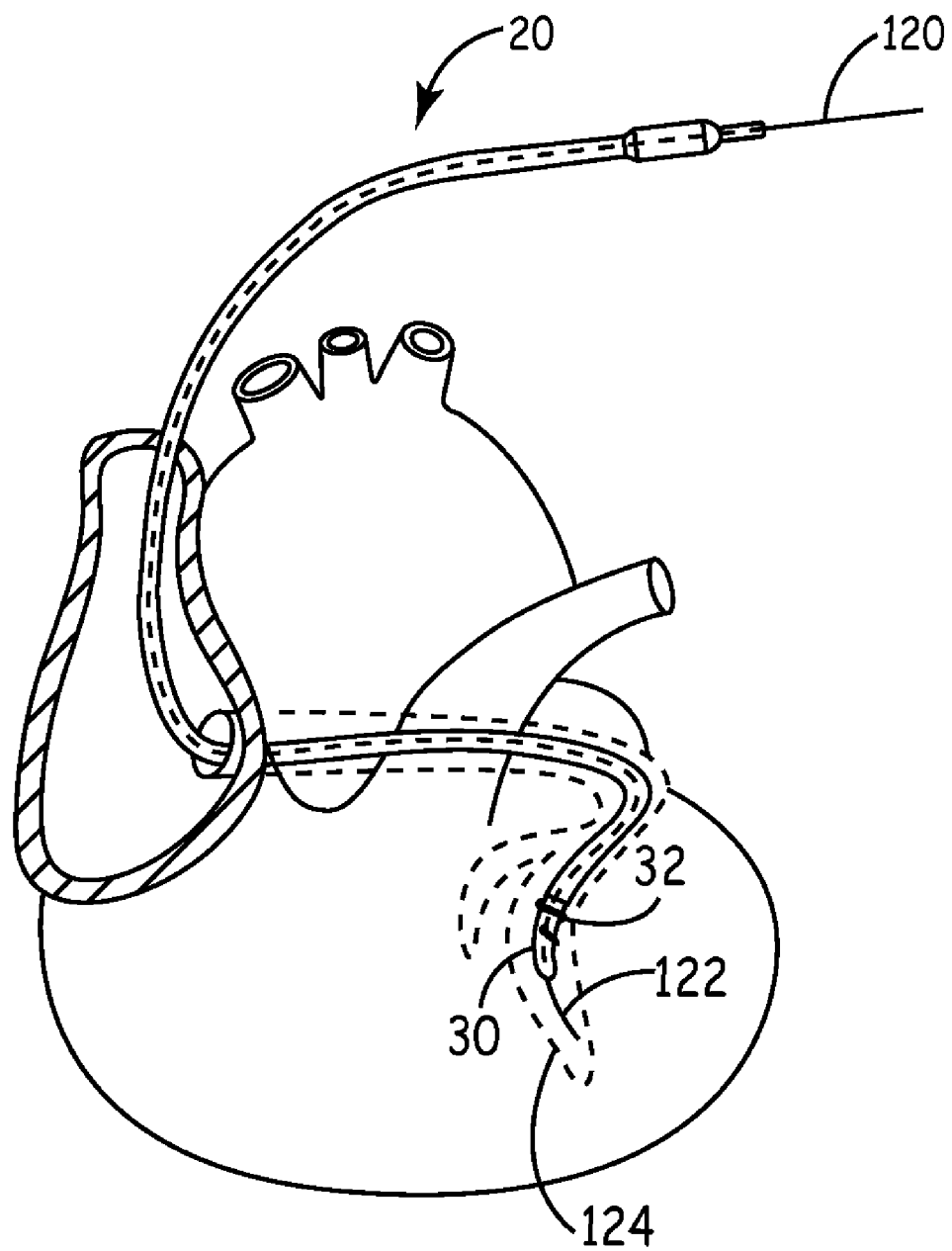
FIG. 12 illustrates a method for deploying an elongated medical device in accordance with an embodiment of the present invention.

FIG. 12 illustrates a method for deploying elongated medical device 20. In this example, elongated medical device 20 is embodied as a coronary sinus lead as shown previously in FIG. 1. Medical device 20 is deployed to a cardiac vein location with the use of a guide wire 120. Similar guide wire assisted procedures may be used for deployment of an elongated medical device in other body locations. In an implantation procedure, guide wire 120 is advanced to a desired implant site. In the example shown in FIG. 12, guide wire 120 is advanced via the coronary sinus to a desired implant site in a cardiac vein 124, over the left ventricle. Elongated medical device 20 is advanced to the implant site by advancing device 20 over the guide wire 120. Elongated medical device 20 may also be deployed with the use of a guide catheter.

Figure 13A:
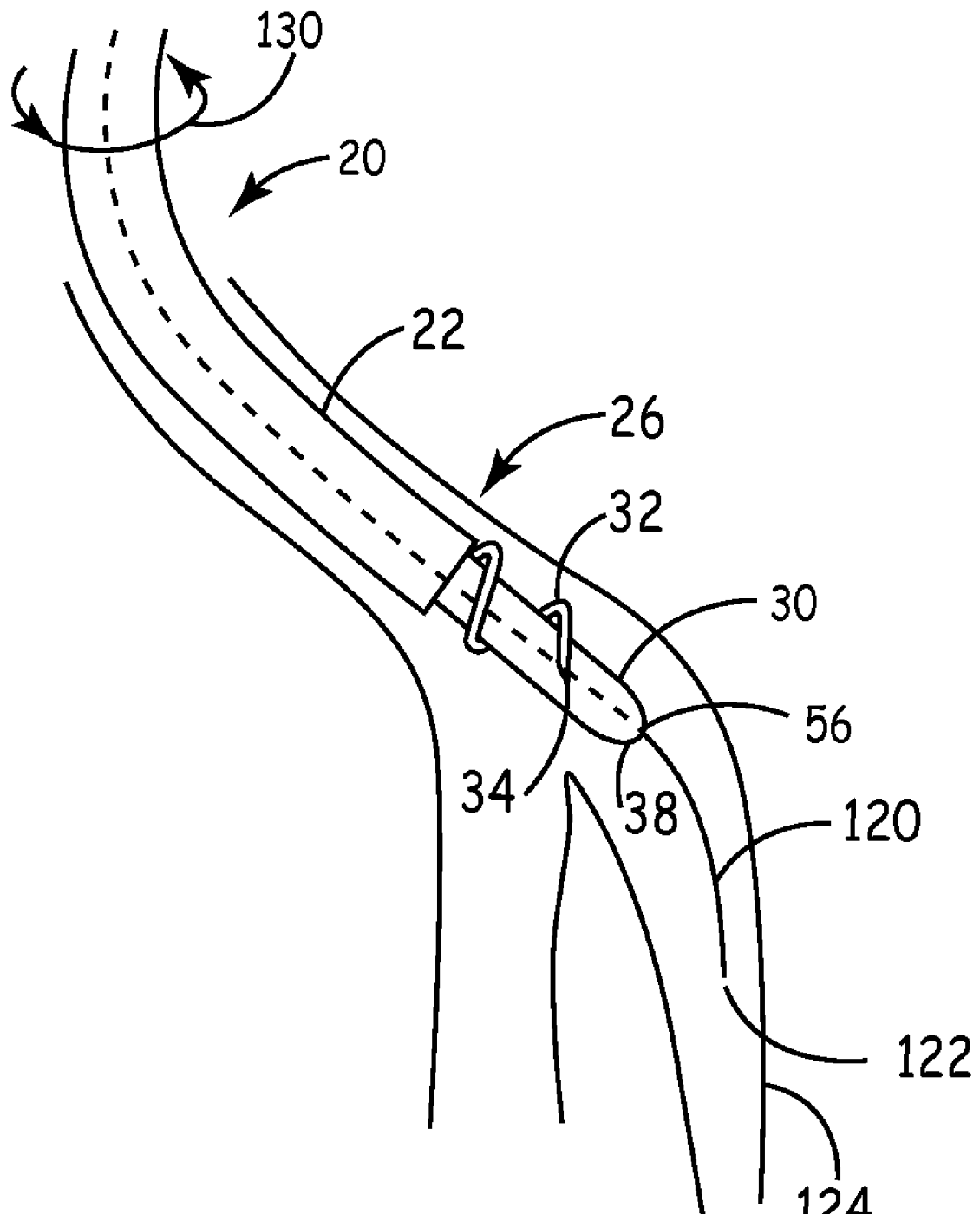
FIG. 13A is an enlarged view of an elongated medical device being advanced into a cardiac vein over guide wire according to an embodiment of the present invention.

FIG. 13A is an enlarged view of the elongated medical device 20 being advanced into a cardiac vein 124 over guide wire 120. As elongated medical device 20 is advanced over guide wire 120, device 20 is counter-rotated as indicated by arrow 130 to prevent tissue-piercing distal tip 34 of helical fixation member 32 from snagging or catching on tissue or anatomical structures along the implantation pathway. Elongated medical device body 22 is provided with a torsional stiffness adequate to transfer rotational motion from the proximal end 24 (shown in FIG. 2) to the distal end 26 of elongated medical device 20. Tracking member 30 extending distally from helical fixation member 32, promotes the safe passage of helical fixation member 32 along the implant pathway.

Tracking member 30 is provided as a flexible member for tracking the guide wire 120 to the implant site while protecting helical fixation member 32 from catching or snagging on tissue as device 20 is advanced. When welding sleeve 44 (shown in FIG. 5) is used in assembling elongated device 20, welding sleeve 44 creates a relatively stiff segment near distal end 26 of elongated body 22. The stiff segment near distal end 26 associated with a relatively rigid welding sleeve assembly may not track well along a tortuous implantation pathway. By providing tracking member 30 as a flexible member, elongated medical device 20 can be passed over a guide wire and follow a tortuous pathway to an implant site.

Tracking member 30 may be formed having a variable stiffness optimized for flexibly tracking a tortuous implantation pathway and promoting smooth advancement over a guide wire while protecting helical fixation member 32 from becoming caught on body tissue or anatomical structures and thereby causing tissue injury or becoming damaged or distorted. A relatively more flexible distal end 38 of tracking member 30 can help to prevent buckling of tracking member 30 over guide wire 120 as elongated medical device 20 is advanced over guide wire 120. Greater flexibility near tracking member distal end 38 improves the ability to maneuver tracking member 30 into selected vein branches.

Figure 13B:
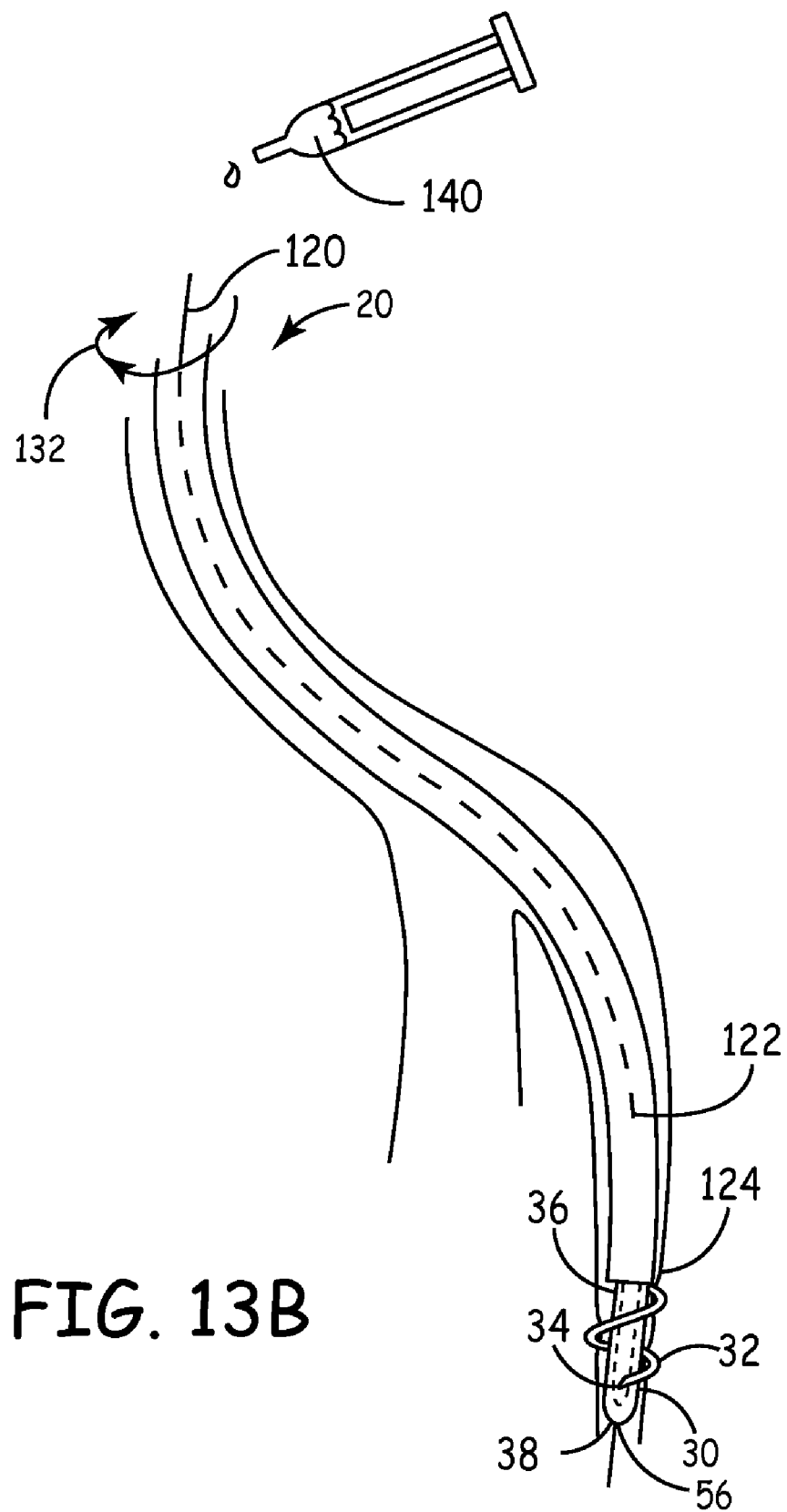
FIG. 13B illustrates fixation of a elongated medical device at the targeted implant site in vein according to an embodiment of the present invention.

FIG. 13B illustrates fixation of the elongated medical device 20 at the targeted implant site in vein 124. After advancing device 20 to a targeted implant site, fluoroscopic imaging, electrophysiological measurements or other testing may be performed to verify acceptable positioning of elongated medical device 20. In some embodiments, a radioopaque or other imaging contrast solution 140 may be injected through the lumen 23 (shown in FIG. 5) of elongated medical device 20 out distal tracking member passage 56 to allow visualization and verification of the anatomical location of tracking member 30 and helical fixation member 32.

Once elongated medical device 20 is positioned at the targeted implant site, device 20 is rotated at its proximal end in the direction indicated by arrow 132 to cause tissue-piercing distal tip 34 to engage and enter the wall of vein 124. Fixation of helical fixation member 32 is achieved by further rotation of elongated medical device 20 in direction 132. The wall of vein 124 will become engaged in the gap formed by distance 36 between tracking member 30 and helical fixation member 32. As helical fixation member 32 becomes fixed within the wall of vein 124, torsional resistance will increase and be transferred along elongated medical device body 22 from distal end 26 to the proximal end of elongated medical device 20. The transfer of increasing torsional resistance provides tactile feedback to the implanting clinician, indicating fixation of helical fixation member 32 in body tissue. Upon verification of acceptable implantation of the distal end 26 of medical device 20, guide wire 120 can be withdrawn and removed from device 20.

Injection of an imaging contrast agent 140 can be also be used to verify fixation of helical member 32. Injection of a radio-opaque contract solution causes residual staining of the tissue engaged in the gap formed by distance 36. As such, visualization of the residual staining of engaged tissue under fluoroscopy can be used to verify fixation of helical member 32. Contrast agent 140 can be flushed away by injecting sterile saline through elongated body lumen 23 after imaging is completed.

Figure 14:
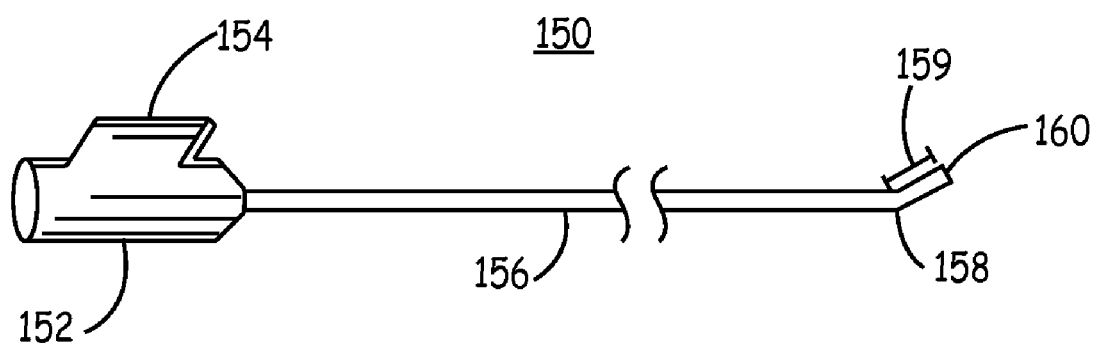
FIG. 14 is a plan view of a stylet that may be used in combination with an elongated medical device according to an embodiment of the present invention.

FIG. 14 is a plan view of a stylet that may be used in combination with an elongated medical device. Stylet 150 is provided with an elongated body 156 with a preformed bend or angle 158. Angle 158 is located a distance 159 from distal end 160 of stylet 150 that is slightly greater than the "stiff" distal segment of the corresponding elongated medical device corresponding to the location of a welding assembly. Stylet 150 is provided with a proximal handle 152. Handle 152 is provided with a marker 154, which may be a physical or printed feature on handle 152, to indicate the plane of angle 158. As shown in FIG. 14, marker 154 is a radial protrusion extending from handle 152 in the plane corresponding to angle 158.

Figure 15A:
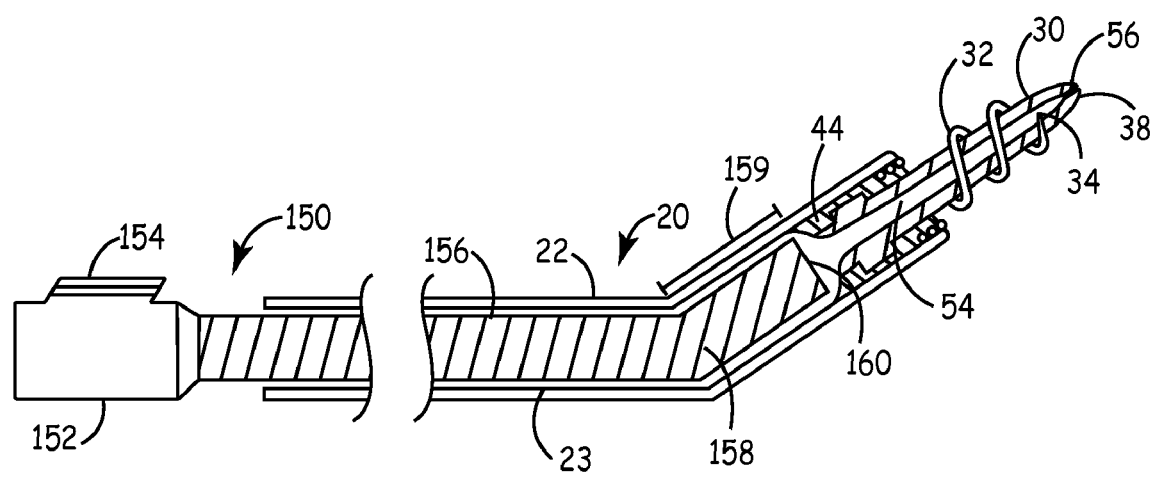
FIG. 15A is a sectional view of an elongated medical device showing a stylet fully inserted in the device according to an embodiment of the present invention.

FIG. 15A is a sectional view of elongated medical device 20 showing stylet 150 fully inserted in device 20. Pre-formed angle 158 causes elongated medical device 20 to bend at a location proximal to the relative stiff distal segment corresponding to welding sleeve 44. Distance 159 between preformed angle 158 and stylet distal end 160 is designed to cause elongated medical device 20 to bend at flexible portion of body 22. Stylet body 156 is formed with a diameter greater than the diameter of tracking member lumen 54 such that the proximal face 78 of tracking member 30 interfaces with stylet distal end 160, acting as a mechanical stop to prevent overadvancement of stylet 150 into device 20.

Marker 154 indicates to an implanting clinician the direction that tracking member 30 is directed when stylet 150 is fully inserted in elongated medical device 20. Thus stylet 150 can be used to facilitate steering of elongated medical device along a desired implant pathway. For example, use of stylet 150 may facilitate sub-selection of cardiac veins when advancing elongated medical device 20 to a desired cardiac vein implant site. A set of stylets could be provided, each having a pre-formed angle of a different degree, to facilitate maneuvering of elongated medical device 20 around different angles, bends or other obstructions encountered along an implantation pathway.

Moreover, stylet 150 can be used to direct tissue-piercing distal tip 34 of helical fixation member 32 toward targeted tissue at an implant site. In the example of the cardiac vein implant site, angle 158 may be positioned to preferentially direct tissue-piercing distal tip 34 into the myocardium.

Figure 15B:
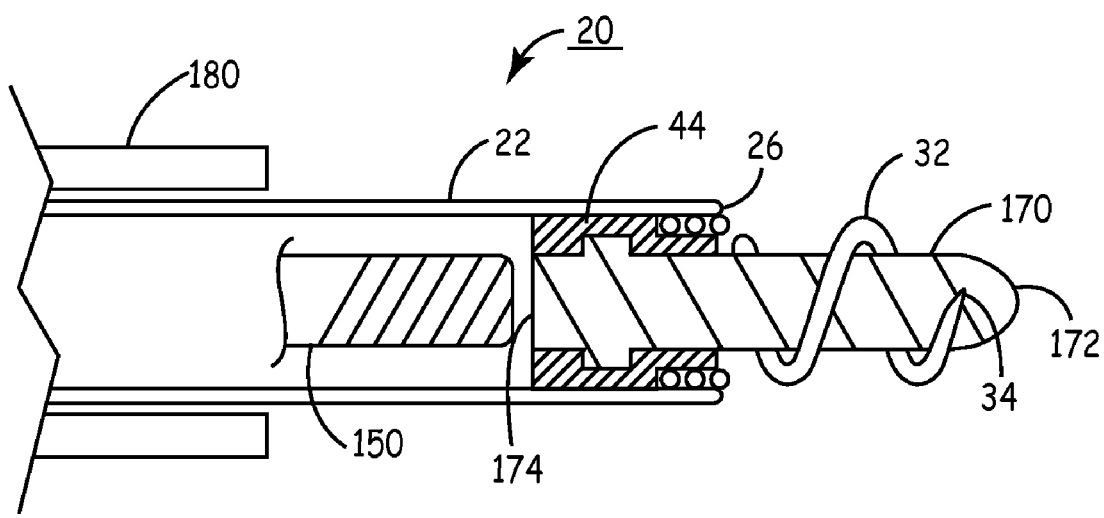
FIG. 15B is a sectional view of a distal portion of an elongated medical device provided with a solid tracking member according to an embodiment of the present invention.

FIG. 15B is a sectional view of the distal portion of elongated medical device 20 provided with a solid tracking member 170. In applications that do not require passing an elongated member out the distal end 172 of tracking member 170, tracking member 170 can be provided as a solid member, without a distal passage. Stylet 150 is advanced up to proximal end 174 of tracking member 170 to facilitate steering of tracking member 170 around obstacles and orienting tissue-piercing distal tip 34 toward a targeted implant site. Elongated device 20 may be implanted with the aid of a guide catheter 180. The use of a guide catheter for steering catheters or leads to a targeted internal body site is known in the art.

Figure 16:
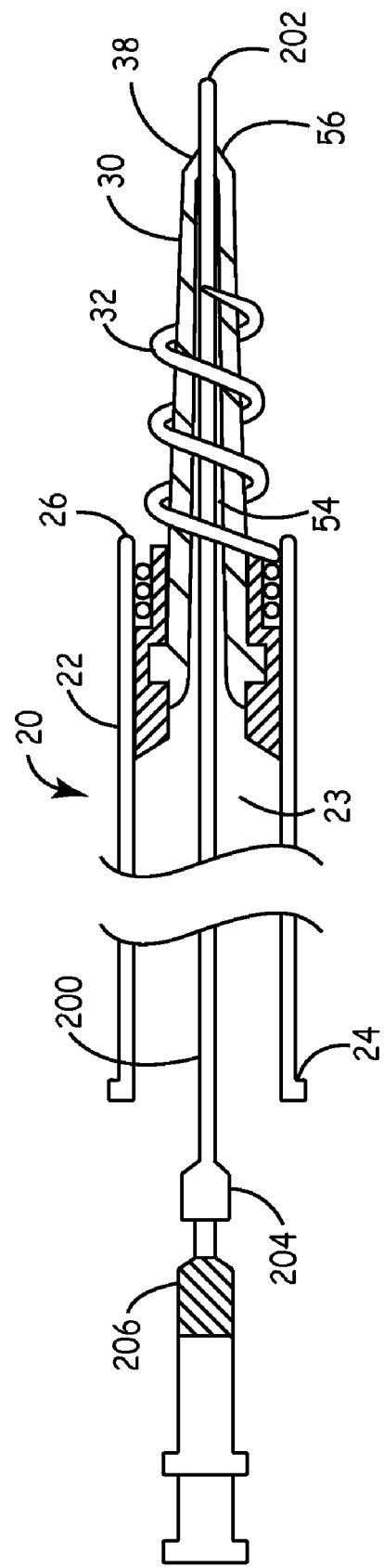
FIG. 16 is a sectional view of an elongated medical device and a microcatheter extending there through for use in local administration of a fluid agent according to an embodiment of the present invention.

FIG. 16 is a sectional view of elongated medical device 20 and a microcatheter for use in local administration of a fluid agent. Microcatheter 200 can be advanced through elongated device body lumen 23, through tracking member lumen 54, and out distal end 38 of tracking member 30 through passage 56. The proximal end 204 of microcatheter 200 is adapted to accept injection, manually or with the use of a pump, of a fluid agent 206 from a fluid reservoir. Fluid agent 206 which may be, for example, a pharmacological, biologic or genetic agent or an imaging contrast agent. Fluid agent 206 exits microcatheter distal end 202. Elongated medical device 20 may thus be used in local delivery of a fluid agent for therapeutic or imaging purposes.

An elongated medical device has been presented in the foregoing description with reference to specific embodiments. It is appreciated that various modifications to the referenced embodiments may be made without departing from the scope of the invention as set forth in the following claims.

What is claimed is:

1. A medical electrical lead comprising:
   an elongated body having a proximal end and a distal end;
   a helical fixation member extending from the distal end of the elongated body, the helical fixation member having a distal tip for fixedly engaging the distal end of the elongated body at an implant site, and
   a tracking member extending from the distal end of the elongated body and extending through the helical fixation member and outward from the distal tip of the helical fixation member,
   wherein the tracking member having a proximal portion extending out from the elongated body distal end having an outer diameter, and the helical fixation member having a corresponding proximal portion extending out from the elongated body distal end; and
   wherein the helical fixation member includes a first winding diameter along a proximal portion of the helical fixation member extending from the elongated body distal end and a second winding diameter, greater than the first winding diameter, along a distal portion of the helical fixation member,
   a tissue engaging gap extending along the second winding diameter of the distal portion of the helical fixation member,
   the helical fixation member proximal portion having the first winding diameter forming a mechanical stop for resisting further advancement of the helical fixation member into the tissue.

2. The medical electrical lead of claim 1, wherein the tracking member includes a substantially circular cross-section.

3. The medical electrical lead of claim 1, wherein the tracking member is a drug-eluting member.

4. The medical electrical lead of claim 1, wherein the helical fixation member is formed having a winding pitch and the distal tip of the helical fixation member is canted with respect to the winding pitch 5. The medical electrical lead of claim 1, wherein the elongated body includes a lumen extending from the proximal end of the elongated body to the distal end of the elongated body to receive one of an elongated member and a fluid and the tracking member comprises a lumen in communication with the elongated body lumen.

6. The medical electrical lead of claim 1, wherein the elongated member is a stylet having a preformed angle to control an orientation of the tracking member.

7. The medical electrical lead of claim 6, wherein the elongated member is a stylet having a preformed angle to control an orientation of the distal tip of the helical fixation member toward the implant site.

8. The medical electrical lead of claim 1, wherein the predetermined distance being about constant along a linear portion of the helical fixation member extending proximally from the helical fixation member distal tip.

9. A medical electrical lead comprising:
   an elongated body having a proximal end and a distal end;
   a helical fixation member extending from the distal end of the elongated body, the helical fixation member having a distal tip for fixedly engaging the distal end of the elongated body at an implant site, and
   a tracking member extending from the distal end of the elongated body and extending through the helical fixation member and outward from the distal tip of the helical fixation member,
   wherein the tracking member having a proximal portion extending out from the elongated body distal end having an outer diameter, and the helical fixation member having a corresponding proximal portion extending out from the elongated body distal end; and
   wherein the helical fixation member includes a final winding adjacent the distal tip and at least one proximal winding, the final winding and the at least one proximal winding being non-concentric.

10. A medical electrical lead comprising:
    an elongated body having a proximal end and a distal end;
    a helical fixation member extending from the distal end of the elongated body, the helical fixation member having a distal tip for fixedly engaging the distal end of the elongated body at an implant site, and
    a tracking member extending from the distal end of the elongated body and extending through the helical fixation member and outward from the distal tip of the helical fixation member,
    wherein the tracking member haying a proximal portion extending out from the elongated body distal end having an outer diameter, and the helical fixation member having a corresponding proximal portion extending out from the elongated body distal end; and
    wherein the tracking member is formed having a D-shape cross-section.

11. An implantable medical device system, comprising:

an elongated body having a proximal end and a distal end;

a helical fixation member extending from the distal end of the elongated body, the helical fixation member having a distal tip for fixedly engaging the distal end of the elongated body at an implant site, and a tracking member extending from the distal end of the elongated body and extending through the helical fixation member and outward from the distal tip of the helical fixation member, the tracking member including an outer surface and the helical fixation member including an inner surface adjacent to and spaced a predetermined distance from the outer surface of the tracking member to form a tissue engaging gap between the helical fixation member and the tracking member for controlling a depth of body tissue engaged in the tissue engaging gap at the implant site; and wherein the helical fixation member includes a first winding diameter along a proximal portion of the helical fixation member extending from the distal end of the elongated body and a second winding diameter, greater than the first winding diameter, along a distal portion of the helical fixation member.

12. The device of claim 11, wherein the tracking member includes a first outer diameter along at least a distal portion of the helical fixation member and a second outer diameter along other than the distal portion of the helical fixation member, the second diameter being greater than the first diameter.

13. The device of claim 11, wherein the tracking member includes a first portion having a first stiffness and a second portion having a second stiffness not equal to the first stiffness.

* * * * *